United States Patent
Ersue et al.

(10) Patent No.: US 7,499,812 B2
(45) Date of Patent: Mar. 3, 2009

(54) METHOD FOR LOCATING FLAWS, AND A MARKING SYSTEM

(75) Inventors: Enis Ersue, Darmstadt (DE); Stephan Wienand, Zwingenberg (DE); Horst Knoche, Biedenkopf (DE)

(73) Assignee: Isra Vision Systems AG, Darmstadt (DE)

( * ) Notice: Subject to any disclaimer, the term of this patent is extended or adjusted under 35 U.S.C. 154(b) by 0 days.

(21) Appl. No.: 10/589,371

(22) PCT Filed: Feb. 10, 2005

(86) PCT No.: PCT/EP2005/001312

§ 371 (c)(1),
(2), (4) Date: Apr. 9, 2007

(87) PCT Pub. No.: WO2005/090907

PCT Pub. Date: Sep. 29, 2005

(65) Prior Publication Data

US 2008/0040059 A1    Feb. 14, 2008

(30) Foreign Application Priority Data

Feb. 18, 2004  (DE) ............ 10 2004 007 830

(51) Int. Cl.
  *G01B 5/28* (2006.01)
(52) U.S. Cl. ............ 702/35; 250/559.25; 356/237.2; 451/103
(58) Field of Classification Search ............ 702/81–83, 702/127, 35; 148/196; 250/259.22; 348/92, 348/128; 356/237.2, 394; 382/141, 152; 451/103

See application file for complete search history.

(56) References Cited

U.S. PATENT DOCUMENTS

| 5,625,197 | A | * | 4/1997 | Shimbara | ............ | 250/559.22 |
| 5,716,262 | A | * | 2/1998 | Kiba | ............ | 451/103 |
| 6,266,138 | B1 | | 7/2001 | Keshavmurthy | ......... | 356/237.2 |
| 6,320,654 | B1 | | 11/2001 | Alders et al. | ............ | 356/237.2 |
| 2003/0139836 | A1 | | 7/2003 | Matthews et al. | | |

FOREIGN PATENT DOCUMENTS

| DE | 197 30 885 | 1/1999 |
| DE | 198 49 802 | 5/2000 |
| DE | 197 39 250 | 1/2003 |
| EP | 1 092 973 | 4/2001 |
| WO | 87/00629 | 1/1987 |

OTHER PUBLICATIONS

ABIS "Automatic Body Inspection System". Steinbichler. Anlage D 7.2. Published Feb. 17, 2000.

* cited by examiner

*Primary Examiner*—John H Le
(74) *Attorney, Agent, or Firm*—Michael J. Striker

(57) ABSTRACT

In the method for locating flaws on the surface of a three-dimensional object the flaws are detected and located using one or more optical image-taking device. When a picture is taken showing a flaw the location of the flaw on the object is determined with great accuracy from the design data for the object, the optical imaging properties of the optical image-taking device, and the positions of the optical image-taking device and the object. A marking system for marking the position of the flaws on the object, which are detected by the method, is also described, which includes plural marking heads and displacement devices for positioning and/or activating the marking heads independently of each other.

8 Claims, 1 Drawing Sheet

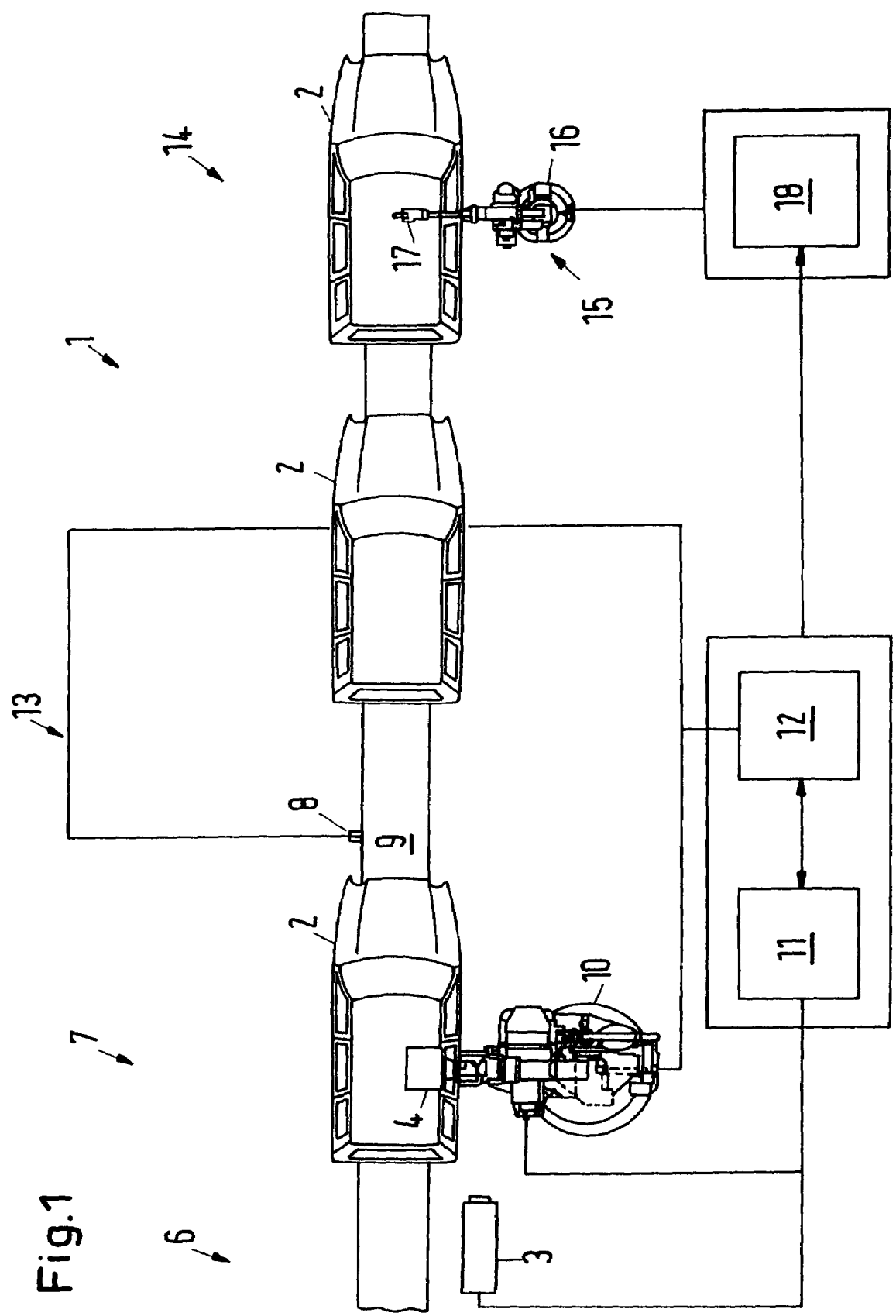

METHOD FOR LOCATING FLAWS, AND A MARKING SYSTEM

CROSS-REFERENCE

This is the U.S. National Stage of PCT/EP 2005/001312, filed on Feb. 10, 2005, in Europe. The invention described and claimed herein below is also described in DE 10 2004 007 830.0, filed on Feb. 18, 2004 in Germany, which provides the basis for a claim of priority of invention under 35 U.S.C. 365 (b).

BACKGROUND OF THE INVENTION

1. The Field of the Invention

The present invention relates to a method for locating flaws on a three-dimensional object, particularly on its surface, the flaws being detected and located using an optical picture-taking device, and to a corresponding marking system. The present invention is suited for use, e.g., to detect painting flaws.

2. Description of Related Art

Inspection systems of this type, e.g., to inspect painted surfaces of bodies, are already known. With the known systems, however, it is difficult to also locate or mark the flaw—which has already been detected—on the object with sufficient precision, since inaccuracies occur in assigning the position of the flaw to the object.

SUMMARY OF THE INVENTION

The object of the present invention is to provide a possibility for locating and, optionally, marking a flaw detected on a three-dimensional object with a high level of accuracy.

This object is essentially attained using a method of the type described initially by the fact that the design data related to the object, the optical imaging properties of the picture-taking device, and the position of the optical picture-taking device and the object are known when the picture is taken, and the fact that the location of the flaw on the object is determined therefrom. With known methods, the location of a detected flaw is determined independently of the object in the three-dimensional space of the inspection system. The flaw must either be marked immediately, or the movement of the object must be traced exactly, so that the flaw can also be located and marked later. Since transporting the three-dimensional objects can always result in unpredicted and undetected displacements, this method is very inaccurate. According to the present invention, it is provided to determine the location of the flaw directly on the object relative to its coordinates or at defined reference points on the object. This is possible, because, in addition to the optical imaging properties of the picture-taking device, the position of the optical picture-taking device and the object when the pictures are taken, the design data related to the object are also known in electronic form, so that the location of the flaw on the three-dimensional object can be unambiguously assigned to a specified position on the object. As a result, once a flaw has been located, it can be reliably found again if the spacial assignment of the object to the inspection system becomes lost. In this case, it is only necessary to remeasure the position of the object.

To this end, the location of the flaw is preferably determined in the coordinate system of the object, which is preferably the coordinate system of the design data or the CAD data and/or data determined using sensors. The location of the flaw relative to the object is determined exactly in the coordinate system of the design data, which renders it unnecessary to trace the movement of the object in space exactly in order to subsequently locate the flaw, optionally mark it, and/or automatically eliminate it. The design data can already be known, e.g., as CAD data used to design the object. It is also possible, according to the present invention, to create the relevant design data based on sensor data, e.g., by taking pictures and evaluating them, via scanning or the like. In this case, it is possible for the necessary design data related to the object to be learned automatically, rendering it unnecessary to specify them separately or to know them in advance. The data are then stored automatically. The determination of the design data from the sensor data can also be used to improve the accuracy of existing design data or to improve their resolution.

In a preferred refinement of the inventive method, the location of the flaw is transferred to a marking device, which marks the location of the flaw on the object. When the evaluation device of the picture-taking device not only detects the flaw but also classifies it, it is possible to apply a different marking depending on the flaw type, so that the flaw type can be identified based on the marking. This is particularly advantageous in terms of easily and quickly reprocessing the flaws, to eliminate them. In addition, according to the present invention, the markings can be applied not exactly on the flaw, but next to the flaw, in order to not cover it. The direction and extent of the displacement preferably depends on the position of the flaw on the object.

According to the present invention, it can also be provided that the start path for the marking device is automatically determined based on the design data related to the object, on position data and/or previously-defined, permissible areas of movement of the marking device. In particular, the marking device can be installed on a displacement device, on which it is possible to easily move the marking device in various degrees of freedom in space. The displacement device can be, e.g., a robot, a manipulator, a handling device, or a multiaxial traveling unit with defined axes of motion. As a result, it is possible to automatically calculate, for the marking device, a collision-free start path to the marking position based on the design or CAD data related to the object and previously-defined, permissible working areas of the displacement devices.

In addition to marking the locations of flaws on the three-dimensional object itself, it is also possible according to the present invention to display the locations of flaws on a display, particularly in a print-out or on a screen. This serves to document the flaws and creates a simple overview of all flaws. If the picture-taking device has determined a flaw type, the flaw type can also be indicated.

To further increase the accuracy of locating flaws on the object, the optical picture-taking device can be calibrated three-dimensionally, and the position of the object can be determined exactly by comparing design data and pictures that were taken. Using this type of fine-positioning, it is possible to very exactly assign the flaws identified in the pictures that were taken to the design data related to the three-dimensional object. The marking device or a marking system can also include an optical picture-taking device, so the object can be fine-positioned relative to the marking device in this manner. This can be particularly important when it is necessary to mark the flaws with high precision or, for other reasons, to perform control with great accuracy. In particular, the object, the picture-taking device and, optionally, one or more displacement devices can be calibrated three-dimensionally to each other, so that their positions in a coordinate system relative to each other are known.

The present invention also relates to a system for marking flaws on an object detected in an inspection that is particulary suited for carrying out the method described above. The marking system includes a marking head and a displacement device, the displacement device positions the marking head at the locations of the flaws based on the design data related to the object and transmitted position data related to the flaw locations. As a result, it is always possible to accurately assign the locations of the flaws to the three-dimensional object. According to the present invention, the marking system can be combined particularly advantageously with an inspection system that determines the location of a known flaw on the object, or in the coordinate system of the design data related to the object or relative to certain reference points on the object.

According to a particular embodiment of the inventive marking system, several marking heads can be provided that are capable of being positioned and/or activated independently of each other. By subdividing the marking system into several subsystems, it is possible to mark the flaw locations on the three-dimensional object particularly quickly, since the subsystems can work in parallel with each other in particular.

As a continuation of this inventive idea, a large number of marking heads can be provided and distributed—and located in fixed positions, in particular—over an area of the object that will possibly be marked, the displacement device specifying, e.g., only the distance of a marking head to be activated from the object. An arrangement of this type can extend, e.g., over the entire width and/or height of the object to be marked, the marking heads being located such that they cover the entire object or the areas thereon that may be marked. With an object that is moved transversely to the position of the marking heads, it is only necessary to wait for the correct point in time before activating the suitable marking head. To this end, it can be moved from one direction of motion to an optimum distance from the surface to be marked in order to perform the marking. With flat surfaces in particular, all marking heads can also be fixed in position, and the distance of all marking heads can be adjusted using the displacement device. This can also be carried out once manually depending on the design data related to the object, if the distance of the marking heads need not be changed for objects of the same type. In that case, the corresponding marking head need be activated only when the object that is moved relative to the marking head is in the correct position. The marking system described above uses the principle of a matrix printer. To also allow the position of the marking head to be corrected in the object's direction of motion, the displacement device can also include a certain amount of play in the object's direction of motion.

To this end, to control the displacement device of the marking heads based on the design data, a control device can automatically assign the location of the flaw to a marking head, which will apply the marking. The system or the motion sequence can be optimized such that all markings to be applied can be applied to the object in the shortest amount of time possible, without the subsystems interfering with each other. To minimize the risk of the subsystems interfering with each other, the various subsystems of the marking system can be located on various sides of the three-dimensional object.

BRIEF DESCRIPTION OF THE DRAWING

Further advantages, features, and possible applications of the present invention also result from the following description of an exemplary embodiment with reference to the drawing. All of the features described and/or depicted graphically are part of the present invention, independently of their wording in the claims or their back-references.

DETAILED DESCRIPTION OF THE INVENTION

FIG. 1 shows an inventive system for locating flaws on a three-dimensional object.

System 1 shown in FIG. 1 for locating flaws on a three-dimensional object 2, in particular on its surfaces, includes an inspection system 13 for detecting and locating flaws on an object 2 using an optical picture-taking device 3, 4 and a subsequent marking system 14, with which the flaws detected in the inspection are marked on the three-dimensional object 2.

System 1 is designed, e.g., to examine a painted surface of bodies, as object 2 to be inspected. It includes several optical picture-taking devices 3, 4, which are combined with illumination devices to form several inspection units located at separate points. Stationary inspection unit 3 is a first subsystem 6 for examining the sides of body 2, and a small-surface area or large-surface area inspection unit 4 is a second subsystem 7 for examining the rest of the surface areas. It is also possible to provide further subsystems and to adapt the size of the inspection units to the particular circumstances. Subsystems 6, 7 are located one behind the other along a displacement device 9—designed as a conveyor belt—for body 2, so that body 2 is moved relative to stationary picture-taking device 3 and, e.g., small-surface area or large-surface area picture-taking devices 4.

In addition, picture-taking device 4 is mounted on a displacement device 10 assigned to it, which allows picture-taking device 4 to attain any possible orientation in space. Displacement device 10 is designed as a manipulator that allows picture-taking device 4 to be moved in several degrees of freedom around various axes of rotation.

By way of body 2 moved on conveyor belt 9 and via manipulator 10 with picture-taking device 4, a relative motion between picture-taking devices 3, 4 and picture-taking devices 3, 4 and illumination devices combined into inspection units, and body 2 is produced, whereby pictures are taken of the areas to be inspected on the surface of body 2 at various points in time using the optical picture-taking devices 3, 4. The pictures that are taken are analyzed in an evaluation device 11 with the aid of image-evaluation algorithms.

To coordinate the relative motion between three-dimensional object 2 and picture-taking devices 3, 4 and the illumination devices of the inspection units, a control device 12 is provided that is set up such that a picture-taking device 3, 4, an illumination device, and the surface are brought into at least one defined geometric relationship with each other during the inspection of each area to be inspected on the surface of body 2, at least for the period of time required to take a picture. To this end, control device 12 knows, e.g., by performing a measurement with a sensor 8, the positions of body 2 moving on conveyor belt 9, and picture-taking devices 3, 4. Picture-taking device 4 mounted on manipulator 10 can also be brought into a specified position by control device 12 relative to the position of body 2, in which the defined geometric relationship between the surface of body 2 and the optical picture-taking device 4 and the illumination device of the inspection unit is attained. The orientation of the surface of object 2 is preferably known from the design data, CAD data, in particular—which are available in electronic form, for example—and/or from the data determined using sensors. When this relationship is attained, a picture is taken of the area to be inspected, and the picture is evaluated by evaluation device 11.

When a flaw on the surface of object 2 is identified in the image evaluation, the location of the flaw on object 2 itself is determined based on the design data of object 2, the optical imaging properties of picture-taking devices 3, 4, and the position of optical picture-taking devices 3, 4 and object 2 when the picture is taken. The location of the flaw in the coordinate system of the design data is determined such that the flaw location is located in a coordinate system relative to the object itself. This has the decisive advantage that the location of the flaw is known relative to the features of object 2 for downstream systems, e.g., a marking system, so that the location of the flaw on object 2 can always be determined very accurately.

It is therefore easily possible to mark the flaws identified during the inspection with a marking device 15 using a marking system 14 located after inspection system 13. To this end, marking device 15 includes a displacement device 16 designed as a manipulator, on which, e.g., a marking head 17 designed as a spray head is located. Displacement device 16 and marking head 17 are controlled using a marking control 18 that is connected with control device 12 of inspection system 13. Several marking devices can also be provided, as an option.

Since body 2 has been transported via conveyor belt 9 from inspection system 13 to marking system 14, the position coordinates of body 2 can also be determined for marking system 14 with the aid of position information related to conveyor belt 9. Marking control 18 receives this information from control device 12. The same applies for the position data related to the locations of flaws on object 2, which were determined by evaluation device 11. It is also possible, of course, to newly determine the position coordinates of body 2 in marking system 14, e.g., via measurement and/or fine-positioning using a picture-taking device in marking system 14, and via evaluation of pronounced features of object 2 known from the design data.

When there are several marking heads 17 that are positionable independently of each other in particular, it is provided that marking control 17 automatically assigns the location of the flaw to a marking head 17 based on the design data related to object 2, and marking head 17 marks the flaw.

In addition, flaw classifications carried out by evaluation device 11 can be forwarded to marking control 18, so that different types of flaws can be characterized on object 2 using different markings by marking heads 17.

The inventive method and the corresponding system with inspection system 13 and marking system 14 have the particular advantage that the locations of flaws relative to the object itself are determined, so that the flaw locations can always be easily assigned to the surface of object 2. This is advantageous for marking, in particular.

REFERENCE NUMERALS

1 System
2 Three-dimensional object, body
3, 4 Optical picture-taking device
6, 7 Subsystems
8 Sensor
9 Displacement device, conveyor belt
10 Displacement device, manipulator
11 Evaluation device
12 Control device
13 Inspection system
14 Marking system
15 Marking devices
16 Displacement device, manipulator
17 Marking head
18 Marking control

What is claimed is:

1. A method for locating and marking flaws on a surface of a three-dimensional object (2), said method comprising the steps of:
    a) detecting and locating at least one flaw on the surface of the three-dimensional object by taking at least one picture with at least one optical image-taking device (3,4), so that the at least one flaw appears in the at least one picture;
    b) determining at least one location of the at least flaw on the surface of the three-dimensional object from the at least one picture using design data related to the object (2), optical imaging properties of the at least one optical image-taking device (3, 4), and a position of the at least one optical image-taking device (3, 4) and a position of the object (2) when the at least one picture is taken;
    c) transferring the at least one location of the at least one flaw determined in step b) to a marking device (15);
    d) determining a start path traversable by the marking device (15) from the design data related to the object (2), from position data and from previously-defined, permissible areas of movement of the marking device (15);
    e) moving the marking device (15) over the object (2) to the at least one location of the at least one flaw; and then
    f) marking the at least one location of the at least one flaw on the object (2) with the marking device (15);
    wherein the at least one optical image-taking device (3, 4), the object (2) and at least one of respective displacement devices (9, 10, 16) for moving the at least one optical image-taking device (3,4), the object (2), and the marking device (15) are three-dimensionally calibrated to each other.

2. The method as defined in claim 1, wherein the at least one location of the at least one flaw is determined with reference to a coordinate system of the object (2).

3. The method as defined in claim 2, wherein the coordinate system is a coordinate system of the design data.

4. The method as defined in claim 1, wherein the at least one location of the at least one flaw is displayed on a display.

5. The method as defined in claim 4, wherein the display is a print-out of a printer or a display screen.

6. The method as recited in claim 1, wherein the position of the object (2) is exactly determined by comparing the design data and pictures that were taken by the at least one optical image-taking device (3, 4).

7. A marking system for flaws on an object, which are identified during an inspection, said marking system comprising
    a marking device (15), said marking device including a plurality of marking heads (17) that are activated independently of each other and a plurality of displacement devices (16) for positioning the marking heads independently of each other; and
    a marking controller (18) connected with the marking device (15);
    wherein said marking controller (18) automatically assigns at least one location of at least one of the flaws to at least one of the marking heads (17) according to design data for the object, said marking controller (18) controls the displacement devices (16) to position said at least one of said marking heads (17) at said at least one location of said at least one flaw based on said design data related to the object (2) and transmitted position data related to said at least one location of said at least one flaw and said marking controller (18) determines a start path for the marking device (15) from said design data related to the object (2), from position data and from previously-defined, permissible areas of movement of the marking device (15).

8. The marking system as defined in claim 7, wherein the marking heads (17) are distributed over an area of the object that may be marked and the displacement devices (16) specify distances from the object (2) at which the marking heads (17) are be activated.

* * * * *